United States Patent
Wagner et al.

(10) Patent No.: US 7,432,400 B2
(45) Date of Patent: Oct. 7, 2008

(54) BIPHENYLENE COMPOUNDS

(75) Inventors: Barbara Wagner, Lörrach (DE); Dietmar Hüglin, Weil am Rhein (DE)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 848 days.

(21) Appl. No.: 10/488,452

(22) PCT Filed: Aug. 29, 2002

(86) PCT No.: PCT/EP02/09627

§ 371 (c)(1),
(2), (4) Date: Mar. 3, 2004

(87) PCT Pub. No.: WO03/022790

PCT Pub. Date: Mar. 20, 2003

(65) Prior Publication Data

US 2004/0265248 A1 Dec. 30, 2004

(30) Foreign Application Priority Data

Sep. 7, 2001 (EP) .................. 01810861
Jun. 20, 2002 (CH) ................... 1059/02

(51) Int. Cl.
C07C 45/00 (2006.01)
C07C 49/00 (2006.01)
A61K 8/00 (2006.01)

(52) U.S. Cl. ........................ 568/312; 568/325; 562/499; 424/59; 424/60

(58) Field of Classification Search ........................ None
See application file for complete search history.

(56) References Cited

U.S. PATENT DOCUMENTS 4,726,942 A   2/1988   Lang et al. ..................... 424/47

FOREIGN PATENT DOCUMENTS

WO   WO00/20384   *   4/2000

OTHER PUBLICATIONS

Fukuda et al. Novel Seco Cyclopropa[c] pyrrolo[3,2-e] indole Bisalkylators Bearing a 3,3'-Arylenebisacryloyl Group as a Linker. Journal of Medicinal Chemistry, 2001, vol. 44, pp. 1396-1406.*
N. Ganushchak et al., Journal of Organic Chemistry of the USSR, vol. 18, No. 8, (1982), pp. 1508-1512.

* cited by examiner

Primary Examiner—Sikarl A Witherspoon
(74) Attorney, Agent, or Firm—Mervin G. Wood

(57) ABSTRACT

These are described biphenylene compounds of formula (I) wherein $R_1$ is a $C_1$-$C_{18}$alkyl, $C_2$-$C_{18}$alkenyl, $C_6$-$C_{10}$aryl or $C_6$-$C_{10}$aryl or $C_6$-$C_{10}$heteroaryl radical each unsubstituted or mono- or poly-substituted by hydroxy, halogen, $C_1$-$C_{18}$alkyl, $C_1$-$C_{18}$alkoxy, amino, $C_1$-$C_5$monoalkyamino or by di-$C_1$-$C_5$alkylamino; $C_5$-$C_7$cycloalkyl or $C_5$-$C_7$cycloalkenyl each unsubstituted or substituted by $C_1$-$C_5$alkyl; —OR'; or NR'R''; $R_2$ is a $C_1$-$C_{18}$alkyl, $C_2$-$C_{18}$alkenyl, $C_6$-$C_{10}$aryl or $C_6$-$C_{10}$heteroaryl radical each unsubstituted or mono- poly-substituted by hydroxy, hadroxy, $C_1$-$C_{18}$alkoxy, amino, $C_1$-$C_5$monoalkylamino or by di-$C_1$-$C_5$alkylamino; —OR'; —NR'R''; or $R_1$ and $R_2$ together form a 5- to 7- membered monocyclic carbocyclic or heterocyclic ring; $R_3$ is hydrogen; $C_1$-$C_6$alkyl or $C_1$-$C_6$alkoxy; R' and R'' are each independently of the other hydrogen; unsubstituted or mono- or poly-hydroxy-, halo-, $C_1$-$C_{18}$alkyl-, $C_1$-$C_{18}$alkoxy-, amino- or quaternary ammonium groupsubstituted $C_1$-$C_{18}$alkyl, $C_5$-$C_7$cycloalkyl or phenyl; and n is 0 or 1; wherein, when $R_2$ is OR' or NR'R'' and n=1, $R_1$ is not simultaneously OR'; or NR'R''. The compounds according to the invention are suitable especially as sun protection agents in cosmetic, pharmaceutical and veterinary medicine preparations.

(1)

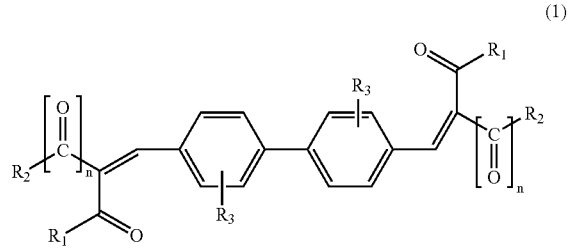

10 Claims, No Drawings

BIPHENYLENE COMPOUNDS

This application is a 371 of international app. No. PCT/EP2002/09627, filed Aug. 29, 2002, which claims priority to EP 01810861.3, filed Sep. 7, 2001.

The present invention relates to novel biphenylene compounds, to a process for their preparation and to the use of such compounds for cosmetic preparations.

The novel biphenylene compounds correspond to the formula

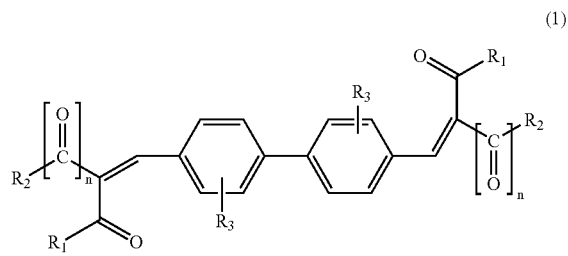

wherein $R_1$ is a $C_1$-$C_{18}$alkyl, $C_2$-$C_{18}$alkenyl, $C_6$-$C_{10}$aryl or $C_6$-$C_{10}$heteroaryl radical each unsubstituted or mono- or poly-substituted by hydroxy, halogen, $C_1$-$C_{18}$alkyl, $C_1$-$C_{18}$alkoxy, amino, $C_1$-$C_5$monoalkylamino or by di-$C_1$-$C_5$alkylamino; $C_5$-$C_7$cycloalkyl or $C_5$-$C_7$cycloalkenyl each unsubstituted or substituted by $C_1$-$C_5$alkyl; —OR'; or —NR'R";

$R_2$ is hydrogen; a $C_1$-$C_{18}$alkyl, $C_2$-$C_{18}$alkenyl, $C_6$-$C_{10}$aryl or $C_6$-$C_{10}$heteroaryl radical each unsubstituted or mono- or poly-substituted by hydroxy, halogen, $C_1$-$C_{18}$alkoxy, amino, $C_1$-$C_5$monoalkylamino or by di-$C_1$-$C_5$alkylamino; —OR'; —NR'R"; or unsubstituted or $C_1$-$C_5$alkyl-substituted —$SO_2$-phenyl; or $R_1$ and $R_2$ together form a 5- to 7-membered monocyclic carbocyclic or heterocyclic ring;

$R_3$ is hydrogen; $C_1$-$C_6$alkyl or $C_1$-$C_6$alkoxy;

R' and R" are each independently of the other hydrogen; unsubstituted or mono- or poly-hydroxy-, halo-, $C_1$-$C_{18}$alkyl-, $C_1$-$C_{18}$alkoxy-, amino- or quaternary ammonium group-substituted $C_1$-$C_{18}$alkyl, $C_5$-$C_7$cycloalkyl or phenyl; and n is 0 or 1;

wherein, when $R_2$ is —OR' or —NR'R" and n=1, $R_1$ is not simultaneously —OR' or —NR'R".

$C_1$-$C_{18}$Alkyl denotes straight-chain and branched hydrocarbon radicals, for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetra-methylbutyl, 1-methylheptyl, 3-methylheptyl, n-octyl, 2-ethylhexyl, 1,1,3trimethylhexyl, 1,1,3,3-tetramethylpentyl, nonyl, decyl, undecyl, 1-methylundecyl, dodecyl, tridecyl, tetradecyl, pentadecyl or hexadecyl or octadecyl.

$C_1$-$C_{18}$Alkoxy denotes straight-chain and branched radicals, for example methoxy, ethoxy, n-propoxy, isopropoxy, n-butoxy, sec-butoxy, tert-butoxy, amyloxy, isoamyloxy or tert-amyloxy, n-hexyloxy, 1-methylhexyloxy, n-heptyloxy, isoheptyloxy, 1,1,3,3-tetramethylbutyloxy, 1-methylheptyloxy, 3-methylheptyloxy, n-octyloxy, 2-ethylhexyloxy, 1,1,3trimethylhexyloxy, 1,1,3,3-tetramethylpentyloxy, nonyloxy, decyloxy, undecyloxy, 1-methylundecyloxy, dodecyloxy, tridecyloxy, tetradecyloxy, pentadecyloxy, hexadecyloxy or octadecyloxy.

$C_2$-$C_{18}$Alkenyl is, for example, allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyt, n-dodec-2-enyl or n-octadec-4-enyl.

$C_6$-$C_{10}$Aryl is, for example, phenyl or naphthyl.

A heterocyclic ring is a heteroaromatic system that contains at least one oxygen, sulfur and/or nitrogen hetero atom in the ring structure.

Preferred heteroaryl groups preferably contain from 2 to 15 carbon atoms.

Examples of mono- and di-$C_1$-$C_5$alkylamino are methylamino, ethylamino, propylamino, n-butylamino, sec-butylamino, tert-butylamino, pentylamino, dimethylamino, diethylamino, dipropylamino, dibutylamino and methylethylamino.

Preference is given to diphenyl compounds of formula (1) wherein $R_1$ and $R_2$ are each independently of the other unsubstituted or $C_1$-$C_5$alkyl-, $C_1$-$C_5$alkoxy-, hydroxy- or halo-substituted $C_1$-$C_{18}$alkyl or phenyl; —OR'; or —NR'R"; or $R_1$ and $R_2$ together form a 5- to 7-membered carbocyclic or heterocyclic ring.

In formula (1)

$R_1$ is preferably $C_1$-$C_5$alkyl; $C_1$-$C_5$alkoxy; phenyl unsubstituted or substituted by $C_1$-$C_5$alkyl, $C_1$-$C_5$alkoxy, hydroxy or by halogen; amino; mono- or di-$C_1$-$C_5$alkylamino.

In formula (1)

$R_2$ is preferably $C_1$-$C_5$alkyl; $C_1$-$C_5$alkoxy; phenyl unsubstituted or substituted by hydroxy, $C_1$-$C_5$alkyl, $C_1$-$C_5$alkoxy or by halogen; amino; mono- or di-$C_1$-$C_5$alkylamino; and n is 0.

Preference is given to compounds of formula (1) wherein $R_1$ and $R_2$ together form a —$(CH_2)_{2-6}$— radical that is not further substituted or is substituted by one or more $C_1$-$C_5$alkyl and is uninterrupted or interrupted by one or two —O— and/or —NH— groups and/or

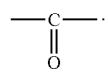

Very special preference is given to compounds of formula (1) wherein $R_1$ and $R_2$ together form an unsubstituted or $C_1$-$C_{10}$alkyl-substituted —$(CH_2)_4$— radical.

Preference is given also to compounds of formula (1) wherein $R_1$ and $R_2$ together form the radical

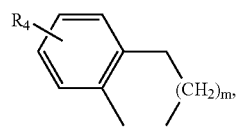

wherein $R_4$ is hydrogen, $C_1$-$C_{10}$alkyl or $C_1$-$C_{10}$alkoxy; and m is 0 or 1.

$R_3$ in formula (1) is preferably hydrogen.

Examples of compounds according to the invention are listed in the following Table 1:

TABLE 1

| Compound of formula | R₁ | R₂ |
|---|---|---|
| (2) | | |
| (3) | | |
| (4) | | |
| (5) | | |
| (6) | *—C₆H₄—F | **—H |
| (7) | | |
| (8) | | |
| (9) | *—C₆H₅ | **—CH₃ |
| (10) | *—C₆H₅ | **—C₆H₅ |
| (11) | | |
| (12) | *—O—C(CH₃)₃ | **—C(=O)CH₃ |
| (13) | *—O—C₂H₅ | **—C₆H₅ |
| (14) | | |
| (15) | | |
| (16) | | |
| (17) | hexyl—O—* | **—S(=O)₂—C₆H₅ |

The compounds of formula (1) are prepared in a manner known per se, as described, for example, in U.S. Pat. No. 4,726,942; DE 3 403 846 A1, FR 8 301 715 or WO 00/20384 A1. The compounds of formula (1) can be prepared, for example, by reacting a diphenylbisaldehyde of formula

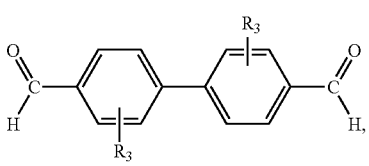

in the presence of a base or acid, with a compound of formula

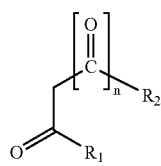

$R_1$, $R_2$, $R_3$ and n are as defined for formula (1).

The reaction is especially carried out in dimethyl sulfoxide, N-methylpyrrolidone, dimethyl-formamide or dimethylacetamide. It is also possible, however, to use protic solvents, such as methanol, ethanol, isobutanol or isopropanol. The reaction can also be carried out in an allphatic or aromatic solvent, such as hexane, toluene or xylene. It is also possible to use an ether, such as diethyl ether and tetrahydrofuran, or a halogenated solvent, such as chloroform or dichloromethane. Mixtures of solvents can also be used.

As base there can preferably be used alkali metal alcoholates, for example sodium methanolate, sodium ethanolate or potassium tert-butanolate, or alkali metal hydroxides, such as sodium hydroxide or potassium hydroxide. Basic ion exchangers can also be used.

As acids there can be used organic and inorganic Bronstedt or Lewis acids or a mixture thereof. Examples of typical acids are hydrochloric acid, sulfuric acid and phosphoric acid. Also effective are Lewis acids, such as aluminium chloride, iron chloride, zinc chloride and potassium fluoride. It is also possible to use acidic Ion exchangers.

The reaction can be carried out at temperatures of from 0° C. to the boiling point of the reaction mixture; it is preferred to carry out the reaction at from 25 to 60° C.

Generally, about from 1.5 to 3.5 mol of the keto compound of formula (1c) are used, based on 1 mol of the compound-of formula (1).

The invention relates also to the process for the preparation of the compounds of formula (1).

The compounds, according to the invention, of formula

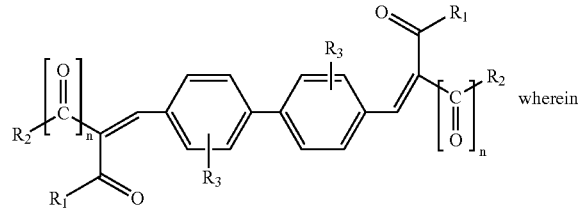

$R_1$ is a $C_1$-$C_{18}$alkyl, $C_2$-$C_{18}$alkenyl, $C_6$-$C_{10}$aryl or $C_6$-$C_{10}$heteroaryl radical each unsubstituted or mono- or poly-substituted by hydroxy, halogen, $C_1$-$C_{18}$alkyl, $C_1$-$C_{18}$alkoxy, amino, $C_1$-$C_5$monoalkylamino or by di-$C_1$-$C_5$alkylamino; $C_5$-$C_7$cycloalkyl or $C_5C_7$cycloalkenyl each unsubstituted or substituted by $C_1$-$C_5$alkyl; —OR'; or —NR'R'';

$R_2$ is hydrogen; a $C_1$-$C_{18}$alkyl, $C_2$-$C_{18}$alkenyl, $C_6$-$C_{10}$aryl or $C_6$-$C_{10}$heteroaryl radical each unsubstituted or mono- or poly-substituted by hydroxy, $C_1$-$C_{18}$alkoxy, amino, $C_1$-$C_5$-monoalkylamino or by di-$C_1C_5$alkylamino; —OR'; —NR'R''; or $R_1$ and $R_2$ together form a 5- to 7-membered monocyclic carbocyclic or heterocyclic ring;

$R_3$ is hydrogen; $C_1$-$C_6$alkyl or $C_1$-$C_6$alkoxy;

R' and R'' are each independently of the other hydrogen; unsubstituted or mono- or poly-hydroxy-, halo-, $C_1$-$C_{18}$alkyl-, $C_1$-$C_{18}$alkoxy-, amino- or quaternary ammonium group-substituted $C_1$-$C_{18}$alkyl, $C_5$-$C_7$cycloalkyl or phenyl; and n is 0 or 1;

wherein, when $R_2$ is —OR' or —NR'R'' and n=1, $R_1$ is not simultaneously —OR' or —NR'R''; are suitable especially as UV filters, that is to say for the protection of organic materials that are sensitive to ultraviolet light, especially human and animal skin and hair, against the action of UV radiation. Such compounds are accordingly suitable as light-protective agents in cosmetic, pharmaceutical and veterinary medicine preparations. Such compounds can be used either in the dissolved state or in the micronised state. The invention accordingly relates also to a cosmetic preparation comprising at least one compound of formula (1), and cosmetically tolerable carriers or adjuvants.

The cosmetic preparation may also comprise, in addition to the UV absorber according to the invention, one or more further UV protective agents of the following substance classes:

1. p-aminobenzoic acid derivatives, for example 4-dimethylaminobenzoic acid 2-ethylhexyl ester;
2. salicylic acid derivatives, for example salicylic acid 2-ethylhexyl ester,
3. benzophenone derivatives, for example 2-hydroxy-4-methoxybenzophenone and its 5-sulfonic acid derivative;
4. dibenzoylmethane derivatives, for example 1-(4-tert-butylphenyl)-3-(4-methoxyphenyl)-propane-1,3-dione;
5. diphenylacrylates, for example 2-ethylhexyl 2-cyano-3,3-diphenylacrylate, and 3-(benzo-furanyl) 2-cyanoacrylate;
6. 3-imidazol-4-ylacrylic acid and esters;
7. benzofuran derivatives, especially 2-(p-aminophenyl)benzofuran derivatives, described in EP-A-582 189, U.S. Pat. No. 5,338,539, U.S. Pat. No. 5,518,713 and EP-A-613 893;
8. polymeric UV absorbers, for example the benzylidene malonate derivatives described in EP-A-709 080;
9. cinnamic acid derivatives, for example the 4-methoxycinnamic acid 2-ethylhexyl ester and isoamyl ester or cinnamic acid derivatives disclosed in U.S. Pat. No. 5,601,811 and WO 97/00851;
10. camphor derivatives, for example 3-(4'-methyl)benzylidene-bornan-2-one, 3-benzylidene-bornan-2-one, N-[2(and 4)-2-oxyborn-3-ylidene-methyl)-benzyl]acrylamide polymer, 3-(4'-trimethylammonium)-benzylidene-bornan-2-one methyl sulfate, 3,3'-(1,4-phenylene-dimethine)-bis(7,7-dimethyl-2-oxo-bicyclo[2.2.1]heptane-1-methanesulfonic acid) and salts, 3-(4'-sulfo)benzylidene-bornan-2-one and salts; camphorbenzalkonium methosulfate;
11. hydroxyphenyltriazine compounds, for example 2-(4'-methoxyphenyl)-4,6-bis(2'-hydroxy-4'-n-octyloxyphenyl)-1,3,5-trazine; 2,4-bis{[4-(3-(2-propyloxy)-2-hydroxy-propyloxy)-2-hydroxy]-phenyl}-6-(4-methoxyphenyl)-1,3,5-triazine; 2,4-bis{[4-(2-ethylhexyloxy)-2-hydroxy]-phenyl}-6-[4(2-methoxyethyl-carboxyl)-phenylamino]-1,3,5-triazine; 2,4-bis{[4-(tris(trimethylsilyloxy-silylpropyloxy)-2-hydroxy-phenyl]-6-(4-methoxyphenyl)-1,3,5-triazine; 2,4-bis{[4-(2''-methylpropenyloxy)-2-hydroxy]-phenyl}-6-(4-methoxyphenyl)-1,3,5-triazine; 2,4-bis{[4-(1',1',1',3',5',5',5'-heptamethyltrisilyl-2''-methyl-propyloxy)-2-hydroxy]-phenyl}-6(4-methoxyphenyl)-1,3,5-triazine; 2,4-bis{[4-(3-(2-propyloxy)-2-hydroxy-propyloxy)-2-hydroxy]-phenyl}-6-[4-ethylcarboxy)-phenylamino]-1,3,5-triazine;

12. benzotriazole compounds, for example 2,2'-methylene-bis(6-(2H-benzotriazol-2-yl)-4-(1,1,3,3-tetramethylbutyl)-phenol

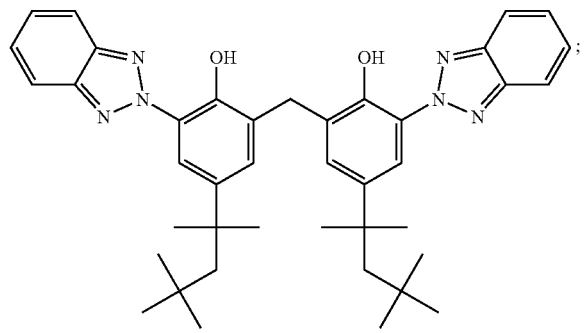

13. trianilino-s-triazine derivatives, for example 2,4,6-trianiline-(p-carbo-2'-ethyl-1'-oxy)-1,3,5-triazine and the UV absorbers disclosed in U.S. Pat. No. 5,332,568, EP-A-517 104, EP-A-507 691, WO 93/17002 and EP-A-570 838;
14. 2-phenylbenzimidazole-5-sulfonic acid and salts thereof;
15. menthyl o-aminobenzoate;
16. $TiO_2$ (variously encapsulated), ZnO and mica.

The UV absorbers described in "Sunscreens", Eds. N. J. Lowe, N. A. Shaath, Marcel Dekker, Inc., New York and Basle or in Cosmetics & Toiletries (107), 50ff (1992) also can be used as additional UV protective substances.

Special preference is given to the light-protective agents indicated in the following Table:

| INCI | Chemical Name | CAS No. |
|---|---|---|
| 3-BENZYLIDENE CAMPHOR | 1,7,7-trimethyl-3-(phenylmethylene)-bicyclo[2.2.1]heptan-2-one | 15087-24-8 |
| 4-METHYLBENZYLIDENE CAMPHOR | (+/−)-1,7,7-trimethyl-3-[(4-methylphenyl)-methylene]bicyclo[2.2.1]heptan-2-one | 36861-47-9 |
| BENZOPHENONE-10 | (2-hydroxy-4-methoxyphenyl)-(4-methylphenyl)methanone | 1641-17-4 |
| BENZOPHENONE-1 | 2,4-dihydroxybenzophenone | 131-56-6 |
| BENZOPHENONE-2 | 2,2',4,4'-tetrahydroxybenzophenone | 131-55-5 |
| BENZOPHENONE-3 | 2-hydroxy-4-methoxybenzophenone | 131-57-7 |
| BENZOPHENONE-4 | 2-hydroxy-4-methoxybenzophenone-5-sulfonic acid | 4065-45-6 |
| BENZOPHENONE-6 | 2,2'-dihydroxy-4,4'-dimethoxybenzophenone | 131-54-4 |
| BENZOPHENONE-8 | 2,2'-dihydroxy-4-methoxybenzophenone | 131-53-3 |
| BENZYLIDENE CAMPHOR SULFONIC ACID | alpha-(2-oxoborn-3-ylidene)-toluene-4-sulfonic acid and its salts | 56039-58-8 |
| BUTYL METHOXY-DIBENZOYLMETHANE | 1-[4-(1,1-dimethylethyl)phenyl]-3-(4-methoxyphenyl)propane-1,3-dione | 70356-09-1 |
| CAMPHOR BENZALKONIUM METHOSULFATE | methyl N,N,N-trimethyl-4-[(4,7,7-trimethyl-3-oxobicyclo[2,2,1]hept-2-ylidene)-methyl]anilinium sulfate | 52793-97-2 |
| CINOXATE | 2-ethoxyethyl p-methoxycinnamate | 104-28-9 |
| DEA-METHOXYCINNAMATE | diethanolamine salt of p-methoxy-hydrocinnamate | 56265-46-4 |
| DIISOPROPYL METHYL CINNAMATE | 2-propenoic acid, 3-[2,4-bis(1-methylethyl)phenyl]-, methyl ester | 32580-71-5 |
| DIPROPYLENE GLYCOL SALICYLATE | dipropylene glycol salicylate | 7491-14-7 |
| ETHYL DIHYDROXYPROPYL PABA | ethyl 4-bis(2-hydroxypropyl)-amino-benzoate | 58882-17-0 |
| ETHYL DIISOPROPYLCINNAMATE | ethyl 3-[2,4-bis(1-methylethyl)phenyl]acrylate | 32580-72-6 |
| ETHYL METHOXYCINNAMATE | ethyl p-methoxycinnamate | 1929-30-2 |
| GLYCERYL OCTANOATE DIMETHOXYCINNAMATE | | |
| GLYCERYL PABA | glyceryl 1-(4-aminobenzoate) | 136-44-7 |
| HOMOSALATE | 3,3,5-trimethylcyclohexyl-2-hydroxy-benzoate | 118-56-9 |
| ISOAMYL p-METHOXY-CINNAMATE | isopentyl p-methoxycinnamate | 71617-10-2 |
| ISOPROPYL DIBENZOYLMETHANE | 1-[4-(1-methylethyl)phenyl]-3-phenyl-propane-1,3-dione | 63250-25-9 |
| ISOPROPYL METHOXYCINNAMATE | isopropyl p-methoxycinnamate | 5466-76-2 |
| LAWSONE | 2-hydroxy-1,4-naphthoquinone | 83-72-7 |
| MENTHYL ANTHRANILATE | menthyl o-aminobenzoate | 134-09-8 |
| MENTHYL SALICYLATE | menthyl salicylate | 89-46-3 |
| OCTOCRYLENE | 2-ethylhexyl 2-cyano-3,3-diphenyl acrylate | 6197-30-4 |
| ETHYLHEXYL DIMETHYL PABA | 2-ethylhexyl 4-(dimethylamino)benzoate | 21245-02-3 |
| ETHYLHEXYL METHOXYCINNAMATE | 2-ethylhexyl 4-methoxycinnamate | 5466-77-3 |
| ETHYLHEXYL SALICYLATE | 2-ethylhexyl salicylate | 118-60-5 |

-continued

| INCI | Chemical Name | CAS No. |
|---|---|---|
| ETHYLHEXYL TRIAZONE | benzoic acid, 4,4',4''-(1,3,5-triazine-2,4,6-triyltriimino)tris-, tris(2-ethylhexyl) ester; 2,4,6-trianilino-(p-carbo-2'-ethylhexyl-1'-oxy)-1,3,5-triazine | 88122-99-0 |
| PABA | 4-aminobenzoic acid | 150-13-0 |
| PEG-25 PABA | benzoic acid, 4-amino-, ethyl ester, polymer with oxirane | 113010-52-9 |
| PENTYL DIMETHYL PABA | amyl dimethyl PABA | 14779-78-3 |
| PHENYLBENZIMIDAZOLE SULFONIC ACID | 2-phenyl-1H-benzimidazole-5-sulfonic acid | 27503-81-7 |
| POLYACRYLAMIDOMETHYL BENZYLIDENE CAMPHOR | | 113783-61-2 |
| TEA-SALICYLATE | triethanolamine salicylate | 2174-16-5 |
| TEREPHTHALYLIDENE DICAMPHOR SULFONIC ACID | 3,3'-(1,4-phenylenedimethylene)bis[7,7-dimethyl-2-oxo-bicyclo[2.2.1]heptane-1-methanesulfonic acid] | 90457-82-2 |
| TITANIUM DIOXIDE | titanium dioxide | 13463-67-7 |
| DIGALLOYL TRIOLEATE | digalloyl trioleate | 17048-39-4 |
| ZINC OXIDE | zinc oxide | 1314-13-2 |
| Methylene bis-benzotriazolyl tetramethylbutylphenol | 2,2'-methylene-bis[6-(2H-benzotriazol-2-yl)-4-(1,1,3,3-tetramethylbutyl)-phenol] | 103597-45-1 |
| Bis-ethylhexyloxyphenol methoxyphenyltriazine | 2,4-bis{[4-(2-ethylhexyloxy)-2-hydroxy]-phenyl}-6-(4-methoxyphenyl)-(1,3,5)-triazine | 187393-00-6 |
| BISIMIDAZYLATE | 1H-benzimidazole-4,6-disulfonic acid, 2,2'-(1,4-phenylene)bis-, disodium salt | 180898-37-7 |
| DIETHYLHEXYL BUTAMIDO TRIAZONE | benzoic acid, 4,4'-[[6-[[(4-[[(1,1-dimethylethyl)-amino]carbonyl]phenyl]amino]-1,3,5-triazine-2,4-diyl]diimino]bis-, bis(2-ethyl-hexyl) ester | 154702-15-5 |
| DROMETRIZOLE TRISILOXANE | phenol, 2-(2H-benzotriazol-2-yl)-4-methyl-6-[2-methyl-3-[1,3,3,3-tetramethyl-1-[(trimethylsilyl)oxy]disiloxanyl]propyl]- | 155633-54-8 |
| BENZYLIDENE MALONATE POLYSILOXANE | alpha-(trimethylsilyl)-omega-(trimethyl-silyloxy)poly[oxy(dimethyl)silylene]-co-[oxy(methyl)(2-{p-[2,2-bis(ethoxy-carbonyl)vinyl]phenoxy}-1-methylene-ethyl)silylene]-co-[oxy(methyl)(2-{p-[2,2-bis(ethoxycarbonyl)vinyl]phenoxy}prop-1-enyl)silylene] | 207574-74-1 |
| | 2-(4-diethylamino-2-hydroxybenzoyl)-benzoic hexyl ester | 302776-68-7 |

Each of the above-mentioned light-protective agents, especially the light-protective agents in the above Table indicated as being preferred, can be used in admixture with the UV absorbers according to the invention. It will be understood in that connection that, in addition to the UV absorbers according to the invention, it is also possible for more than one of the additional light-protective agents to be used, for example, two, three, four, five or six further light-protective agents. Preference is given to the use of mixing ratios of UV absorbers according to the invention/further light-protective agents of from 1:99 to 99:1, especially from 1:95 to 95:1 and preferably from 10:90 to 90:10, based on weight. Of special interest are mixing ratios of from 20:80 to 80:20, especially from 40:60 to 60:40 and preferably of approximately 50:50. Such mixtures can be used, inter alia, to improve solubility or to increase UV absorption.

Appropriate mixtures can be used especially advantageously in a cosmetic composition according to the invention.

The invention relates also to cosmetic compositions that comprise at least one of the UV absorbers according to the invention. The cosmetic compositions are suitable especially as UV filters, that is to say for the protection of organic materials that are sensitive to ultraviolet light, especially skin and hair, against the damaging action of UV radiation.

The UV absorbers can be used either in the dissolved state or in the micronised state.

Any known process suitable for the preparation of microparticles can be used for the preparation of the micronised UV absorbers, for example:
   wet-grinding with a hard grinding medium, for example zirconium silicate and a protective surfactant or a protective polymer in water or in a suitable organic solvent;
   spray-drying from a suitable solvent, for example aqueous suspensions or suspensions containing organic solvents, or true solutions In water, ethanol, dichloroethane, toluene, N-methylpyrrolidone inter alia;
   by the expansion according to the RESS process (Rapid Expansion of Supercritical Solutions) of supercritical fluids (e.g. $CO_2$) in which the UV filter or filters is/are dissolved or the expansion of fluid carbon dioxide together with a solution of one or more UV filters in a suitable organic solvent;
   by reprecipitation from suitable solvents, including supercritical fluids (GASR process=Gas Anti-Solvent Recrystallisation/PCA process=Precipitation with Compressed Antisolvents).

As grinding apparatus for the preparation of the micronised organic UV absorbers there may be used, for example, a jet mill, ball mill, vibratory mill or hammer mill, preferably a high-speed mixing mill. The grinding is preferably carried out with a grinding aid, for example an alkylated vinylpyrrolidone polymer, a vinylpyrrolidone/vinyl acetate copolymer, an acyl glutamate, an alkyl polyglucoside, ceteareth-25 or a phospholipid.

The micronised UV absorbers so obtained usually have an average particle size that is from 0.02 to 2, preferably from 0.05 to 1.5, and more especially from 0.1 to 1.0, nm.

The UV absorbers can also be used dry in powder form. For that purpose the UV absorbers are subjected to known grinding methods, such as vacuum atomization, countercurrent spray-drying etc. Such powders have a particle size of from 0.1 nm to 2 μm. To avoid the occurrence of agglomeration, the UV absorbers can be coated with a surface-active compound prior to the pulverisation process, for example with an anionic, non-ionic or amphoteric surfactant, e.g. a phospholipid or a known polymer, such as PVP, an acrylate etc.

The cosmetic compositions contain, for example, from 0.1 to 30% by weight, preferably from 0.1 to 15% by weight and espedally from 0.5 to 10% by weight, based on the total weight of the composition, of one or more UV absorbers and at least one cosmetically tolerable adjuvant.

The cosmetic compositions can be prepared by physically mixing the UV absorber(s) with the adjuvant using customary methods, for example by simply stirring together the individual components, especially by making use of the dissolution properties of already known cosmetic UV absorbers, for example OMC, salicylic acid isooctyl ester, inter alia. The UV absorber can be used, for example, without further treatment, or in the micronised state, or in the form of a powder.

The cosmetic compositions may be, for example, creams, gels, lotions, alcoholic and aqueous/alcoholic solutions, emulsions, wax/fat compositions, stick preparations, powders or ointments.

As water- and oil-containing emulsions (e.g. W/O, O/W, O/W/O and W/O/W emulsions or microemulsions) the compositions contain, for example, from 0.1 to 30% by weight, preferably from 0.1 to 15% by weight and especially from 0.5 to 10% by weight, based on the total weight of the composition, of one or more UV absorbers, from 1 to 60% by weight, especially from 5 to 50% by weight and preferably from 10 to 35% by weight, based on the total weight of the composition, of at least one oil component, from 0 to 30% by weight, especially from 1 to 30% by weight and preferably from 4 to 20% by weight, based on the total weight of the composition, of at least one emulsifier, from 10 to 90% by weight, especially from 30 to 90% by weight, based on the total weight of the composition, of water, and from 0 to 88.9% by weight, especially from 1 to 50% by weight, of further cosmetically tolerable adjuvants.

As oil components of oil-containing compositions (e.g. oils, W/O, O/W, O/W/O and W/O/W emulsions or microemulsions) there come Into consideration, for example, Guerbet alcohols based on fatty alcohols having from 6 to 18, preferably from 8 to 10, carbon atoms, esters of linear $C_6$-$C_{24}$ fatty acids with linear $C_3$-$C_{24}$ alcohols, esters of branched $C_8$-$C_{13}$ carboxylic acids with linear $C_6$-$C_{24}$ fatty alcohols, esters of linear $C_6$-$C_{24}$ fatty acids with branched alcohols, especially 2-ethylhexanol, esters of hydroxycarboxylic acids with linear or branched $C_6$-$C_{22}$ fatty alcohols, especially dioctyl malates, esters of linear and/or branched fatty acids with polyhydric alcohols (for example propylene glycol, dimer diol or trimer triol) and/or Guerbet alcohols, triglycerides based on $C_6$-$C_{10}$ fatty acids, liquid mono-di-/tri-glyceride mixtures based on $C_6$-$C_{18}$ fatty acids, esters of $C_6$-$C_{24}$ fatty alcohols and/or Guerbet alcohols with aromatic carboxylic acids, especially benzoic acid, esters of $C_2$-$C_{12}$dicarboxylic acids with linear or branched alcohols having from 1 to 22 carbon atoms or polyols having from 2 to 10 carbon atoms and from 2 to 6 hydroxy groups, vegetable oils (such as sunflower oil, olive oil, soybean oil, rapeseed oil, almond oil, jojoba oil, orange oil, wheatgerm oil, peach kernel oil and the liquid components of coconut oil), branched primary alcohols, substituted cyclohexanes, linear and branched $C_6$-$C_{22}$ fatty alcohol carbonates, Guerbet carbonates, esters of benzoic acid with linear and/or branched $C_6$-$C_{22}$ alcohols (e.g. Finsolv® TN), linear or branched, symmetric or asymmetric dialkyl ethers having a total of from 12 to 36 carbon atoms, especially from 12 to 24 carbon atoms, for example di-n-octyl ether, di-n-decyl ether, di-n-nonyl ether, di-n-undecyl ether, di-n-dodecyl ether, n-hexyl n-octyl ether, n-octyl n-decyl ether, n-decyl n-undecyl ether, n-undecyl n-dodecyl ether, n-hexyl n-undecyl ether, di-tert-butyl ether, diisopentyl ether, di-3-ethyidecyl ether, tert-butyl n-octyl ether, isopentyl n-octyl ether and 2-methyl pentyl-n-octyl ether, ring-opening products of epoxidised fatty acid esters with polyols, silicone oils and/or aliphatic or naphthenic hydrocarbons. Also of importance are monoesters of fatty acids with alcohols having from 3 to 24 carbon atoms. That group of substances comprises the esterification products of fatty acids having from 8 to 24 carbon atoms, for example caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and technical-grade mixtures thereof (obtained, for example, in the pressure removal of natural fats and oils, in the reduction of aldehydes from Roelen's oxosynthesis or in the dimerisation of unsaturated fatty acids) with alcohols, for example isopropyl alcohol, caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linoyl alcohol, linolenyl alcohol, elaeostearyl alcohol, arachidyl alcohol, gadoleyl alcohol, behenyl alcohol, erucyl alcohol and brassidyl alcohol and technical-grade mixtures thereof (obtained, for example, in the high-pressure hydrogenation of technical-grade methyl esters based on fats and oils or aldehydes from Roelen's oxosynthesis and as monomer fractions in the dimerisation of unsaturated fatty alcohols). Of special importance are isopropyl myristate, isononanoic acid $C_{16}$-$C_{18}$alkyl esters, stearic acid 2-ethylhexyl ester, cetyl oleate, glycerol tricaprylate, coconut fatty alcohol caprinatelcaprylate and n-butyl stearate. Further oil components that can be used are dicarboxylic acid esters, such as di-n-butyl adipate, di(2-ethylhexyl) adipate, di(2-ethylhexyl) succinate and diisotridecyl acetate, and also diol esters, such as ethylene glycol dioleate, ethylene glycol dilsotridecanoate, propylene glycol di(2-ethylhexanoate), propylene glycol diisostearate, propylene glycol dipelargonate, butanediol diisostearate and neopentyl glycol dicaprylate. Preferred mono- or poly-ols are ethanol, isopropanol, propylene glycol, hexylene glycol, glycerol and sorbitol. It is also possible to use di- and/or tri-valent metal salts (alkaline earth metal, $Al^{3+}$ inter alia) of one or more alkyl-carboxylic acids.

The oil components can be used in an amount of, for example, from 1 to 60% by weight, especially from 5 to 50% by weight and preferably from 10 to 35% by weight, based on the total weight of the composition.

Any conventionally usable emulsifier can be used for the compositions.

As emulsifiers there come into consideration, for example, non-ionic surfactants from the following groups:

addition products of from 2 to 30 mol of ethylene oxide and/or from 0 to 5 mol of propylene oxide with linear fatty alcohols having from 8 to 22 carbon atoms, with fatty acids having from 12 to 22 carbon atoms and with alkylphenols having from 8 to 15 carbon atoms in the alkyl group, for example ceteareth-20 or ceteareth-12;

$C_{12}$-$C_{22}$ fatty acid mono- and di-esters of addition products of from 1 to 30 mol of ethylene oxide with polyols having from 3 to 6 carbon atoms, especially with glycerol;

glycerol mono- and di-esters and sorbitan mono- and di-esters of saturated and unsaturated fatty acids having from 6 to 22 carbon atoms and ethylene oxide addition products thereof, for example glyceryl stearates, glyceryl isostearates, glyceryl oleates, sorbitan oleates or sorbitan sesquioleates;

$C_8$-$C_{22}$alkyl-mono- and -oligo-glycosides and ethoxylated analogues thereof, degrees of oligomerisation of from 1.1 to 5, especially from 1.2 to 1.4, being preferred, and glucose being preferred as the sugar component;

addition products of from 2 to 60 mol, especially from 15 to 60 mol, of ethylene oxide with castor oil and/or hydrogenated castor oil;

polyol esters and especially polyglycerol esters, for example dilsostearoyl polyglyceryl-3-diisostearates, polyglyceryl-3-diisostearates, triglyceryl dilsostearates, polyglyceryl-2-sesquiisostearates or polyglyceryl dimerates. Mixtures of compounds from a plurality of those substance classes are also suitable;

partial esters based on linear, branched, unsaturated or saturated $C_6$-$C_{22}$ fatty acids, ricinoleic acid and also 12-hydroxystearic acid and on glycerol, polyglycerol, pentaerythritol, dipentaerythritol, sugar alcohols (e.g. sorbitol), alkyl glucosides (e.g. methyl glucoside, butyl glucoside, lauryl glucoside) and also polyglucosides (e.g. cellulose), for example polyglyceryl-2-dihydroxystearates or polyglyceryl-2-diricinoleates;

mono-, di- and tri-alkylphosphates and also mono-, di- and/or tri-PEG-alkylphosphates and salts thereof;

wool wax alcohols;

one or more ethoxylated esters of natural derivatives, for example polyethoxylated esters of hydrogenated castor oil;

silicone oil emulsifiers, for example silicone polyol;

polysiloxane/polyalkyl/polyether copolymers and corresponding derivatives, for example cetyl dimethicone copolyol;

mixed esters of pentaerythritol, fatty acids, citric acid and fatty alcohol (see DE-A-1 165 574) and/or mixed esters of fatty acids having from 6 to 22 carbon atoms, methylglucose and polyols, preferably glycerol or polyglycerol, for example polyglyceryl-3-glucose distearates, polyglyderyl-3-glucose dioleates, methyl glucose dioleates or dicocoyl pentaerythryl distearyl citrates and also polyalkylene glycols.

The addition products of ethylene oxide and/or of propylene oxide with fatty alcohols, fatty acids, alkylphenols, glycerol mono- and di-esters and also sorbitan mono- and di-esters of fatty acids, or with castor oil, are known, commercially available products. They are usually homologue mixtures, the average degree of alkoxylation of which corresponds to the ratio of the amounts of ethylene oxide and/or propylene oxide and substrate with which the addition reaction is carried out. $C_{12}$-$C_{18}$ fatty acid mono- and di-esters of addition products of ethylene oxide with glycerol are known, for example, from DE-A-2 024 051 as fat-restoring substances for cosmetic preparations.

$C_8$-$C_{18}$Akyl-mono- and -oligo-glycosides, their preparation and their use are known from the prior art. They are prepared especially by reacting glucose or oligosaccharides with primary alcohols having from 8 to 18 carbon atoms. Suitable glycoside radicals include monoglycosides in which a cyclic sugar radical is glycosidically bonded to the fatty alcohol and also oligomeric glycosides having a degree of oligomerisation of up to preferably about 8.

The degree of oligomerisation is a statistical average value based on a homologue distribution customary for such technical-grade products.

It is also possible to use zwitterionic surfactants as emulsifiers. The term "zwitterionic surfactants" denotes especially surface-active compounds that carry at least one quaternary ammonium group and at least one carboxylate and/or sulfonate group in the molecule. Zwitterionic surfactants that are especially suitable are the so-called betaines, such as N-alkyl-N,N-dimethylammonium glycinates, for example cocoalkyldimethylammonium glycinate, N-acylaminopropyl-N,N-dimethylammonium glycinates, for example cocoacylaminopropyl-dimethylammonium glycinate, and 2-alkyl-3-carboxymethyl-3-hydroxyethylimidazolines each having from 8 to 18 carbon atoms in the alkyl or acyl group and also cocoacylaminoethylhy-droxyethylcarboxymethylglycinate. Special preference is given to the fatty acid amide derivative known by the CTFA name cocamidopropyl betaine. Likewise suitable as emulsifiers are ampholytic surfactants. Ampholytic surfactants are to be understood as meaning especially those which, In addition to containing a $C_8$-$C_{18}$-alkyl or -acyl group, contain at least one free amino group and at least one —COOH or —SO$_3$H group in the molecule and are capable of forming internal salts. Examples of suitable ampholytic surfactants include N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines; 2-alkylaminopropionic acids and alkylaminoacetic acids, each having approximately from 8 to 18 carbon atoms in the alkyl group.

Ampholytic surfactants to which special preference is given are N-cocoalkylamino-proplonate, cocoacylaminoethylaminopropionate and $C_{12}$-$C_{18}$acylsarcosine. In addition to the ampholytic emulsifiers there also come into consideration quaternary emulsifiers, special preference being given to those of the esterquat type, preferably methyl-quaternised di-fatty acid triethanolamine ester salts.

Non-ionic emulsifiers are preferred. Of the non-ionic emulsifiers mentioned, special preference is given to ethoxylated fatty alcohols having from 8 to 22 carbon atoms and from 4 to 30 EO units.

The emulsifiers may be used in an amount of, for example, from 1 to 30% by weight, especially from 4 to 20% by weight and preferably from 5 to 10% by weight, based on the total weight of the composition. It is, however, also possible in principle to dispense with the use of emulsifiers.

The compositions according to the invention, for example creams, gels, lotions, alcoholic and aqueous/alcoholic solutions, emulsions, wax/fat compositions, stick preparations, powders or ointments, may in addition contain, as further adjuvants and additives, mild surfactants, super-fatting agents, pearlescent waxes, consistency regulators, thickeners, polymers, silicone compounds, fats, waxes, stabilisers, biogenic active ingredients, deodorising active ingredients, anti-dandruff agents, film formers, swelling agents, further UV light-protective factors, antioxidants, hydrotropic agents, preservatives, insect repellents, self-tanning agents, solubilisers, perfume oils, colourants, bacteria-inhibiting agents and the like.

Substances suitable for use as super-fatting agents are, for example, lanolin and lecithin and also polyethoxylated or acrylated lanolin and lecithin derivatives, polyol fatty acid esters, monoglycerides and fatty acid alkanolamides, the latter simultaneously acting as foam stabilisers.

Examples of suitable mild surfactants, that is to say surfactants especially well tolerated by the skin, include fatty alcohol polyglycol ether sulfates, monoglyceride sulfates, mono- and/or di-alkyl sulfosuccinates, fatty acid isethionates, fatty acid sarcosinates, fatty acid taurides, fatty acid glutamates, α-olefin sulfonates, ether carboxylic acids, alkyl oligoglucosides, fatty acid glucamides, alkylamidobetaines and/or protein fatty acid condensation products, the latter preferably being based on wheat proteins.

As pearlescent waxes there come into consideration, for example: alkylene glycol esters, especially ethylene glycol distearate; fatty acid alkanolamides, especially coco fatty acid di-ethanolamide; partial glycerides, especially stearic acid monoglyceride; esters of polyvalent, unsubstituted or hydroxy-substituted carboxylic acids with fatty alcohols having from 6 to 22 carbon atoms, especially long-chained esters of tartaric acid; fatty substances, for example fatty alcohols, fatty ketones, fatty aldehydes, fatty ethers and fatty carbonates, which in total have at least 24 carbon atoms, especially laurone and distearyl ether; fatty acids, such as stearic acid, hydroxystearic acid or behenic acid, ring-opening products of olefin epoxides having from 12 to 22 carbon atoms with fatty alcohols having from 12 to 22 carbon atoms and/or polyols having from 2 to 15 carbon atoms and from 2 to 10 hydroxy groups, and mixtures thereof.

As consistency regulators there come into consideration especially fatty alcohols or hydroxy fatty alcohols having from 12 to 22 carbon atoms and preferably from 16 to 18 carbon atoms, and in addition partial glycerides, fatty acids and hydroxy fatty acids. Preference is given to a combination of such substances with alkyl-oligoglucosides and/or fatty acid N-methylglucamides of identical chain length and/or polyglycerol poly-12-hydroxystearates. Suitable thickeners include, for example, Aerosil types (hydrophilic silicic acids), polysaccharides, especially xanthan gum, guar-guar, agar-agar, alginates and Tyloses, carboxymethyl cellulose and hydroxymethyl cellulose, also relatively high molecular weight polyethylene glycol mono- and di-esters of fatty acids, polyacrylates (e.g. Carbopol® from Goodrich or Synthalen® from Sigma), polyacrylamides, polyvinyl alcohol and polyvinylpyrrolidone, surfactants, for example ethoxylated fatty acid glycerides, esters of fatty acids with polyols, for example pentaerythritol or trimethylolpropane, fatty alcohol ethoxylates with restricted homologue distribution and alkyl-oligoglucosides as well as electrolytes, such as sodium chloride or ammonium chloride.

Suitable cationic polymers are, for example, cationic cellulose derivatives, for example a quaternised hydroxymethyl cellulose obtainable under the name Polymer JR 400® from Amerchol, cationic starch, copolymers of diallylammonium salts and acrylamides, quaternised vinylpyrrolidonelinyl imidazole polymers, for example Luviquat® (BASF), condensation products of polyglycols and amines, quatemised collagen polypeptides, for example lauryl-dimonium hydroxypropyl hydrolyzed collagen (Lamequat®L/Grünau), quatemised wheat polypeptides, polyethyleneimine, cationic silicone polymers, for example amidomethicones, copolymers of adipic acid and dimethylaminohydroxypropyidiethylenetriamine (Cartaretin®/Sandoz), copolymers of acrylic acid with dimethyldiallylammonium chloride (Merquat® 550/Chemviron), polyaminopolyamides, as described, for example, In FR-A-2 252 840, and the crosslinked water-soluble polymers thereof, cationic chitin derivatives, for example quatemised chitosan, optionally distributed as microcrystals; condensation products of dihaloalkyls, for example dibromobutane, with bisdialkylamines, for example bisdimethylamino-1,3propane, cationic guar gum, for example Jaguar® C-17, Jaguar® C-16 from Celanese, quatemised ammonium salt polymers, for example Mirapol® A-15, Mirapol® AD-1, Mirapol® AZ-1 from Miranol.

As anionic, zwifterionic, amphoteric and non-ionic polymers there come into consideration, for example, vinyl acetate/crotonic acid copolymers, vinylpyrrolidone/vinyl acrylate copolymers, vinyl acetate/butyl maleate/isobomyl acrylate copolymers, methyl vinyl ether/maleic anhydride copolymers and esters thereof, uncrosslinked polyacrylic acids and polyacrylic acids crosslinked with polyols, acrylamidopropyltrimethylammonium chloride/acrylate copolymers, octyl acrylamide/methyl methacrylate/tert-butylaminoethyl methacrylate/2-hydroxypropyl methacrylate copolymers, polyvinylpyrrolidone, vinylpyrrolidone/vinyl acetate copolymers, vinylpyrrolidone/dimethylaminoethyl methacrylate/vinyl caprolactam terpolymers and also optionally derivatised cellulose ethers and silicones.

Suitable silicone compounds are, for example, dimethylpolysiloxanes, methylphenyl-polysiloxanes, cyclic silicones, and also amino-, fatty acid-, alcohol-, polyether-, epoxy-, fluorine-, glycoside- and/or alkyl-modified silicone compounds, which at room temperature may be in either liquid or resinous form. Also suitable are simethicones, which are mixtures of dimethicones having an average chain length of from 200 to 300 dimethylsiloxane units with hydrogenated silicates. A detailed survey by Todd et al. of suitable volatile silicones may in addition be found in Cosm. Toil. 91, 27 (1976).

Typical examples of fats are glycerides, and as waxes there come into consideration, inter alia, beeswax, camauba wax, candelilla wax, montan wax, paraffin wax, hydrogenated castor oils and fatty acid esters or microwaxes solid at room temperature optionally in combination with hydrophilic waxes, e.g. -cetylstearyl alcohol or partial glycerides. Metal salts of fatty acids, for example magnesium, aluminium and/or zinc stearate or ricinoleate, may be used as stabilisers.

Biogenic active ingredients are to be understood as meaning, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

As deodorising active ingredients there come into consideration, for example, anti-perspirants, for example aluminium chlorohydrates (see J. Soc. Cosm. Chem. 24, 281 (1973)). Under the trade mark Locron® of Hoechst AG, Frankfurt (FRG), there is available commercially, for example, an aluminium chlorohydrate corresponding to formula $Al_2(OH)_5Cl \times 2.5\ H_2O$, the use of which is especially preferred (see J. Pharm. Pharmacol. 26, 531 (1975)). Besides the chlorohydrates, it is also possible to use aluminium hydroxy-acetates and acidic aluminium/zirconium salts. Esterase inhibitors may be added as further deodorising active ingredients. Such inhibitors are preferably trialkyl citrates, such as trimethyl citrate, tripropyl citrate, triisopropyl citrate, tributyl citrate and especially triethyl citrate (Hydagen® CAT, Henkel KGaA Dosseldorf/FRG), which inhibit enzyme activity and hence reduce odour formation. Further substances that come into consideration as esterase inhibitors are sterol sulfates or phosphates, for example lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester and hydroxycarboxylic acids and esters thereof, for example citric acid, malic acid, tartaric acid or tartaric acid diethyl ester. Antibacterial active ingredients that influence the microbial flora and kill, or inhibit the growth of, sweat-decomposing bacteria can likewise be present in the preparations (especially in stick preparations). Examples include chitosan, phenoxyethanol and chlorhexidine gluconate. 5-Chloro-2-(2,4dichlorophenoxy)-phenol (Irgasan®, Ciba Specialty Chemicals Inc.) has also proved especially effective.

As anti-dandruff agents there may be used, for example, dimbazole, octopirox and zinc pyrithione. Customary film formers include, for example, chitosan, microcrystalline chitosan, quatemised chitosan, polyvinylpyrrolidone, vinylpyrrolidone/vinyl acetate copolymers, polymers of quaternary cellulose derivatives containing a high proportion of acrylic acid, collagen, hyaluronic acid and salts thereof and similar compounds. As swelling agents for aqueous phases there may be used montmorillonites, clay mineral substances, Pemulen and also alkyl-modified types of Carbopol (Goodrich). Further suitable polymers and swelling agents can be found in the review by R. Lochhead In Cosm. Toil. 108, 95 (1993).

In addition to the primary light-protective substances Kt is also possible to use secondary light-protective substances of the antioxidant kind which interrupt the photochemical reaction chain triggered when UV radiation penetrates the skin or hair. Typical examples of such antioxidants are amino adds (e.g. glycine, histidine, tyrosine, tryptophan) and derivatives thereof, imidazoles (e.g. urocanic acid) and derivatives thereof, peptides, such as D,L-camosine, D-camosine, L-camosine and derivatives thereof (e.g. anserine), carotinoids, carotenes (e.g. α-carotene, β-carotene, lycopene) and derivatives thereof, chlorogenic acid and derivatives thereof, lipoic acid and derivatives thereof (e.g. dihydrolipoic acid), aurothio-glycose, propylthiouracil and other thiols (e.g. thioredoxin, glutathione, cysteine, cystine, cystamine and the glycosyl, N-acetyl, methyl, ethyl, propyl, amyl, butyl, lauryl, palmitoyl, oleyl, γ-linoleyl, cholesteryl and glyceryl esters thereof) and also salts thereof, dilauryl thiodipropionate, distearyl thiodipropionate, thiodipropionic acid and derivatives thereof (esters, ethers, peptides, lipids, nucleotides, nucleosides and salts) and also sulfoximine compounds (e.g. buthionine sulfoximines, homocysteine sulfoximine, buthionine sulfones, penta-, hexa-, hepta-thionine sulfoximine) in very small tolerable amounts(e.g. from pmol to gmovkg), also (metal) chelating agents (e.g. α-hydroxy fatty acids, palmitic acid, phytic acid, lactoferrin), α-hydroxy acids (e.g. citric add, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic add, oleic acid), folic add and derivatives thereof, ubiquinone and ubiquinol and derivatives thereof, vitamin C and derivatives (e.g. ascorbyl palmitate, magnesium ascorbyl phosphate, ascorbyl acetate), tocopherols and derivatives (e.g. vitamin E acetate), vitamin A and derivatives (e.g. vitamin A palmitate) and also coniferyl benzoate of benzoin resin, rutinic acid and derivatives thereof, α-glycosylrutin, ferulic acid, furfurylidene glucitol, camosine, butyl hydroxytoluene, butyl hydroxyanisole, resinous nordihydrogualaretic acid, nordihydroguaiaretic acid, trihydroxybutyrophenone, uric acid and derivatives thereof, mannose and derivatives thereof, superoxide dismutase, N-[3-(3,5-di-tert-butyl-4-hydroxyphenyl)proplonyl] sulfanilic acid (and salts thereof, for example the sodium salts), zinc and derivatives thereof (e.g. ZnO, $ZnSO_4$), selenium and derivatives thereof (e.g. selenium methionine), stilbene and derivatives thereof (e.g. stilbene oxide, trans-stilbene oxide) and the derivatives suitable according to the invention (salts, esters, ethers, sugars, nucleotides, nucleosides, peptides and lipids) of those mentioned active ingredients. HALS (="Hindered Amine Light Stabilizers") compounds may also be mentioned. The amount of antioxidants present is usually from 0.001 to 30% by weight, preferably from 0.01 to 3% by weight, based on the weight of the UV absorber(s).

To improve the flow behaviour it is also possible to employ hydrotropic agents, for example ethanol, isopropyl alcohol or polyols. The polyols that come into consideration for that purpose have preferably from 2 to 15 carbon atoms and at least two hydroxy groups.

The polyols may also contain further functional groups, especially amino groups, and/or may be modified with nitrogen. Typical examples are as follows:

glycerol;

alkylene glycols, for example ethylene glycol, diethylene glycol, propylene glycol, butylene glycol, hexylene glycol and also polyethylene glycols having an average molecular weight of from 100 to 1000 dalton;

technical oligoglycerol mixtures having an intrinsic degree of condensation of from 1.5 to 10, for example technical diglycerol mixtures having a diglycerol content of from 40 to 50% by weight;

methylol compounds, such as, especially, trimethylolethane, trimethylolpropane, trimethyl-olbutane, pentaerythritol and dipentaerythriftol;

lower alkyl-glucosides, especially those having from 1 to 8 carbon atoms in the alkyl radical, for example methyl and butyl glucoside;

sugar alcohols having from 5 to 12 carbon atoms, for example sorbitol or mannitol;

sugars having from 5 to 12 carbon atoms, for example glucose or saccharose;

amino sugars, for example glucamine;

dialcohol amines, such as diethanolamine or 2-amino-1,3-propanediol.

Suitable preservatives include, for example, phenoxyethanol, formaldehyde solution, Parabens, pentanediol or sorbic acid and the further substance classes listed in Schedule 6, Parts A and B of the Cosmetics Regulations.

There may be mentioned as perfume oils mixtures of natural and/or synthetic aromatic substances. Natural aromatic substances are, for example, extracts from blossom (lilies, lavender, roses, jasmine, neroli, ylang-ylang), from stems and leaves (geranium, patchouli, petitgrain), from fruit (aniseed, coriander, carraway, juniper), from fruit peel (bergamot, lemons, oranges), from roots (mace, angelica, celery, cardamom, costus, iris, calmus), from wood (pinewood, sandalwood, gualacum wood, cedarwood, rosewood), from herbs and grasses (tarragon, lemon grass, sage, thyme), from needles and twigs (spruce, pine, Scots pine, mountain pine), from resins and balsams (galbanum, elemi, benzoin, myrrh, olibanum, opoponax). Animal raw materials also come Into consideration, for example civet and castoreum. Typical synthetic aromatic substances are, for example, products of the ester, ether, aldehyde, ketone, alcohol or hydrocarbon type.

Aromatic substance compounds of the ester type are, for example, benzyl acetate, phenoxyethyl isobutyrate, p-tert-butylcydohexyl acetate, linalyl acetate, dimethyl-benzylcarbinyl acetate, phenylethyl acetate, linalyl benzoate, benzyl formate, ethylmethylphenyl glycinate, allylcyclohexyl propionate, styrallyl propionate and benzyl salicylate. The ethers include, for example, benzyl ethyl ether; the aldehydes include, for example, the linear alkanals having from 8 to 18 hydrocarbon atoms, citral, citronellal, citronellyl oxyacetaldehyde, cyclamen aldehyde, hydroxycitronellal, lilial and bourgeonal; the ketones include, for example, the ionones, α-isomethylionone and methyl cedryl ketone; the alcohols include, for example, anethol, citronellol, eugenol, isoeugenol, geraniol, linalool, phenyl ethyl alcohol and terpinol; and the hydrocarbons include mainly the terpenes and balsams. It is preferable, however, to use mixtures of various aromatic substances that together produce an attractive scent. Ethereal oils of relatively low volatility, which are chiefly used as aroma components, are also suitable as perfume oils, e.g. sage oil, camomile oil, clove oil, melissa oil, oil of cinnamon leaves, lime blossom oil, juniper berry oil, vetiver oil, olibanum oil, galbanum oil, labolanum oil and lavandin oil. Preference is given to the use of bergamot oil, dihydromyrcenol, lilial, lyral, citronellol, phenyl ethyl alcohol, α-hexyl cinnamaldehyde, geraniol, benzyl acetone, cyclamen aidehyde, linalool, boisambrene forte, ambroxan, indole, hedione, sandelice, lemon oil, tangerine oil, orange oil, allyl amyl glycolate, cyclovertal, lavandin oil, muscatel sage oil, β-damascone, bourbon geranium oil, cyclohexyl salicylate, vertofix coeur, iso-E-Super, Fixolide NP, evemyl, iraldein gamma, phenylacetic acid, geranyl acetate, benzyl acetate, rose oxide, romillat, irotyl and floramat alone or in admixture with one another.

There may be used as colourants the substances that are suitable and permitted for cosmetic purposes, as compiled, for example, in the publication "Kosmetische Färbemittel" of the Farbstoffkommission der Deutschen Forschungsgemeinschaft, Verlag Chemie, Weinheim, 1984, pages 81 to 106. The colourants are usually used in concentrations of from 0.001 to 0.1% by weight, based on the total mixture.

Typical examples of bacteria-inhibiting agents are preservatives that have a specific action against gram-positive bacteria, such as 2,4,4'-trichloro-2'-hydroxydiphenyl ether, chlorhexidine (1,6-di(4-chlorophenyl-biguanido)hexane) or TCC (3,4,4'-trichlorocarbanilide).

A large number of aromatic substances and ethereal oils also have antimicrobial properties. Typical examples are the active ingredients eugenol, menthol and thymol in clove oil, mint oil and thyme oil. A natural deodorising agent of interest is the terpene alcohol farnesol (3,7,11-trimethyl-2,6,10-dodecatrien-1-ol), which is present in lime blossom oil. Glycerol monolaurate has also proved to be a bacteriostatic agent. The amount of the additional bacteria-inhibiting agents present is usually from 0.1 to 2% by weight, based on the solids content of the preparations.

It is furthermore possible for the cosmetic compositions to contain, as adjuvants, anti-foams, such as silicones, structurants, such as maleic acid, solubilisers, such as ethylene glycol, propylene glycol, glycerol or diethylene glycol, opacifiers, such as latex, styrene/PVP or styrene/acrylamide copolymers, complexing agents, such as EDTA, NTA, β-alaninediacetic acid or phosphonic acids, propellants, such as propane/butane mixtures, $N_2O$, dimethyl ether, $CO_2$, $N_2$ or air, so-called coupler and developer components as oxidation dye precursors, reducing agents, such as thioglycolic acid and derivatives thereof, thiolactic acid, cysteamine, thiomalic acid or α-mercaptoethanesulfonic acid, or oxidising agents, such as hydrogen peroxide, potassium bromate or sodium bromate.

There come into consideration as insect repellents, for example, N,N-diethyl-m-toluamide, 1,2-pentanediol or insect repellent 3535; suitable self-tanning agents are, for example, dihydroxyacetone, erythrulose or mixtures of dihydroxyacetone and erythrulose.

Cosmetic formulations according to the invention are contained in a wide variety of cosmetic preparations. There come into consideration, for example, especially the following preparations:

skin-care preparations, e.g. skin-washing and cleansing preparations in the form of tablet-form or liquid soaps, synthetic detergents or washing pastes, bath preparations, e.g. liquid (foam baths, milks, shower preparations) or solid bath preparations, e.g. bath cubes and bath salts;

skin-care preparations, e.g. skin emulsions, multi-emulsions or skin oils;

cosmetic personal care preparations, e.g. facial make-up in the form of day creams or powder creams, face powder (loose or pressed), rouge or cream make-up, eye-care preparations, e.g. eyeshadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;

foot-care preparations, e.g. foot baths, foot powders, foot creams or foot balsams, special deodorants and antiperspirants or callus-removing preparations;

light-protective preparations, such as sun milks, lotions, creams or oils, sunblocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or aftershave lotions;

fragrance preparations, e.g. fragrances (eau de Cologne, eau de toilette, eau de parfum, parfum de toilette, perfume), perfume oils or perfume creams;

cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colourants, preparations containing self-oxidising dyes, or natural hair colourants, such as henna or camomile.

The final formulations listed may exist in a wide variety of presentation forms, for example:
- in the form of liquid preparations as a W/O, O/W, O/W/O, W/O/W or PIT emulsion and all kinds of microemulsions,
- in the form of a gel,
- in the form of an oil, a cream, milk or lotion,
- in the form of a powder, a lacquer, a tablet or make-up,
- in the form of a stick,
- in the form of a spray (spray with propellent gas or pump-action spray) or an aerosol,
- in the form of a foam, or
- in the form of a paste.

Of special Importance as cosmetic compositions for the skin are light-protective preparations, such as sun milks, lotions, creams, oils, sunblocks or tropicals, pretanning preparations or after-sun preparations, also skin-tanning preparations, for example self-tanning creams. Of particular interest are sun protection creams, sun protection lotions, sun protection oils, sun protection milk and sun protection preparations in the form of a spray.

Of special importance as cosmetic compositions for the hair are the above-mentioned preparations for hair treatment, especially hair-washing preparations in the form of shampoos, hair conditioners, hair-care preparations, e.g. pretreatment preparations, hair tonics, styling creams, styling gels, pomades, hair rinses, treatment packs, intensive hair treatments, hair-straightening preparations, liquid hair-setting preparations, hair foams and hairsprays. Of special interest are hair-washing preparations in the form of shampoos.

A shampoo has, for example, the following composition: from 0.01 to 5% by weight of a UV absorber according to the invention, 12.0% by weight of sodium laureth-2-sulfate, 4.0% by weight of cocamidopropyl betaine, 3.0% by weight of sodium chloride, and water ad 100%.

For example, especially the following hair-cosmetic formulations may be used:
- $a_1$) spontaneously emulsifying stock formulation, consisting of the UV absorber according to the invention, PEG-6-$C_{10}$oxoalcohol and sorbitan sesquioleate, to which water and any desired quaternary ammonium compound, for example 4% minkamidopropyl-dimethyl-2-hydroxyethylammonium chloride or Quaternium 80 is added;
- $a_2$) spontaneously emulsifying stockformulation consisting of the UV absorber according to the invention, tributyl citrate and PEG-20-sorbitan monooleate, to which water and any desired quaternary ammonium compound, for example 4% minkamidopropyl-dimethyl-2-hydroxyethylammhonium chloride or Quaternium 80 is added;
- b) Quat-doped solutions of the UV absorber according to the invention in butyltriglycol and tributyl citrate;
- c) mixtures or solutions of the UV absorber according to the invention with n-alkylpyrrolidone.

The cosmetic preparation according to the invention contains from 0.1 to 15% by weight, preferably from 0.5 to 10% by weight, based on the total weight of the composition, of a UV absorber of formula (1) or of a mixture of UV absorbers and a cosmetically tolerable adjuvant.

The cosmetic preparation can be prepared by physically mixing the UV absorber or UV absorbers with the adjuvant using conventional methods, for example by simply stirring the individual components together.

The cosmetic preparation according to the invention can be formulated as a water-in-oil or oil-in-water emulsion, as an oil-in-alcohol lotion, as a vesicular dispersion of an ionic or non-ionic amphiphilic lipid, as a gel, solid stick or as an aerosol formulation.

As a water-in-oil or oil-in-water emulsion, the cosmetically tolerable adjuvant preferably contains from 5 to 50% of an oil phase, from 5 to 20% of an emulsifier and from 30 to 90% water. The oil phase can comprise any oil suitable for cosmetic formulations, for example one or more hydrocarbon oils, a wax, a natural oil, a silicone oil, a fatty acid ester or a fatty alcohol. Preferred mono- or poly-ols are ethanol, isopropanol, propylene glycol, hexylene glycol, glycerol and sorbitol.

For the cosmetic preparation according to the invention it is possible to use any conventionally usable emulsifier, for example one or more ethoxylated esters of natural derivatives, for example polyethoxylated esters of hydrogenated castor oil, or a silicone oil emulsifier, for example silicone polyol; an unethoxylated or ethoxylated fatty acid soap; an ethoxylated fatty alcohol; an unethoxylated or ethoxylated sorbitan ester; an ethoxylated fatty acid; or an ethoxylated glyceride.

The cosmetic preparation may also comprise further components, for example emollients, emulsion stabilisers, skin moisturisers, skin-tanning accelerators, thickeners, such as xanthan, moisture retention agents, for example glycerol, preservatives, aromatic substances and colourants.

The cosmetic preparation according to the invention is distinguished by excellent protection of human skin against the damaging effect of sunlight.

In the following Examples percentages relate to weight. The amounts of the biphenylene compounds used relate to the pure substance.

PREPARATION EXAMPLES OF THE NOVEL COMPOUNDS

Parallel Synthesis of the Compounds of Formula

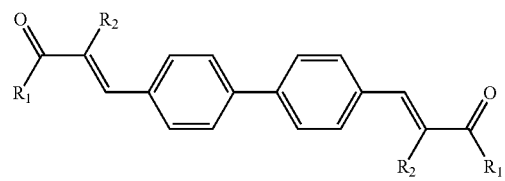

in which the C=C double bond is In the Z or E configuration.

$R_1$ and $R_2$ are as defined in claim 1.

0.0012 mol of a ketone of formula

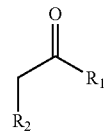

is weighed out, and potassium hydroxide (85%, 79 mg, 0.0012 mol) in 3 ml of ethanol is added. The mixture is stirred for 30 minutes at room temperature, before adding 4,4'-biphenyldicarbaldehyde (97.4%, 0.13 g, 0.0006 mol) dissolved in 2 ml of DMSO. The reaction mixture is stirred for 16 hours at 38° C. After cooling to room temperature, the product is precipitated by the addition of 5 ml of 1M hydrochloric acid. The precipitate is filtered off and washed with copious amounts of water, methanol and finally isobutanol. The product is dried in vacuo at 50° C. Subsequent column chromatography (Nucleosil 5C18)) using a mixture of acetonitrile and water (98:2) yields the pure product.

By way of example, the following Table lists a number of biphenyl compounds according to the invention together with their $\lambda_{max}$ values (measured in acetonitrile 98/water 2).

| Ex. | Ketone used | Comp. of formula | | $\lambda_{max}$ [nm] |
|---|---|---|---|---|
| 1 |  | (2) | 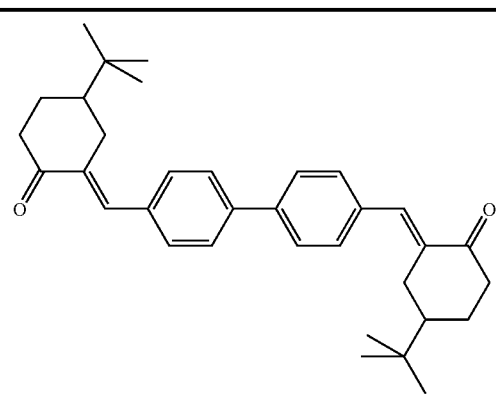 | 357 |
| 2 | 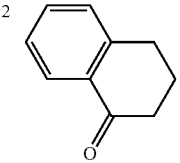 | (3) | 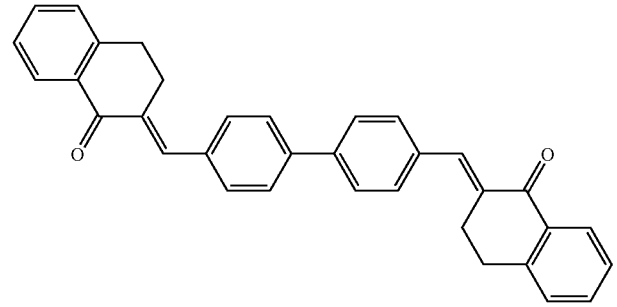 | 351 |
| 3 | 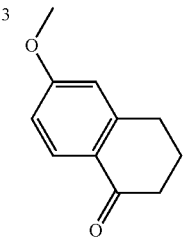 | (4) | 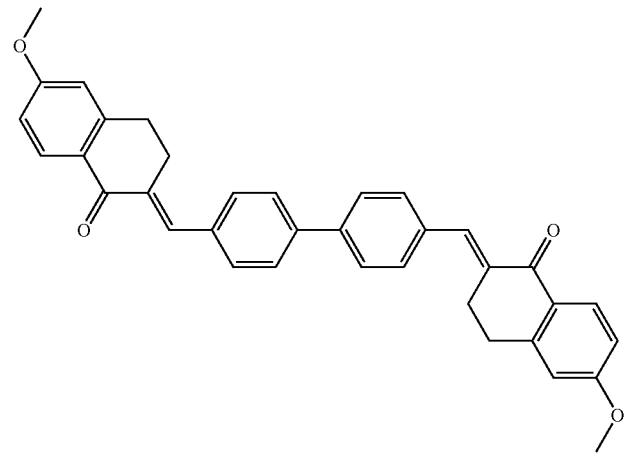 | 351 |

-continued

| Ex. | Ketone used | Comp. of formula | | $\lambda_{max}$ [nm] |
|---|---|---|---|---|
| 4 | (2-hexylcyclopentanone structure) | (5) | (bis-hexyl cyclopentanone biphenyl bis-ylidene structure) | 282 |
| 5 | 4′-fluoroacetophenone | (6) | (bis(4-fluorophenyl) biphenyl bis-enone structure) | 358 |
| 6 | cycloheptanone | (7) | (biphenyl bis(cycloheptanone ylidene) structure) | 337 |

-continued

| Ex. | Ketone used | Comp. of formula | | $\lambda_{max}$ [nm] |
|---|---|---|---|---|
| 7 | cyclooctanone | (8) | bis(cyclooctanone ylidene methyl) biphenyl | 315 |
| 8 | propiophenone | (9) | | 326 |
| 9 | deoxybenzoin | (10) | | 326 |
| 10 | ε-caprolactone | (11) | | 361 |
| 11 | tert-butyl acetoacetate | (12) | | 345 |

Example 13

Preparation of the Compound of Formula

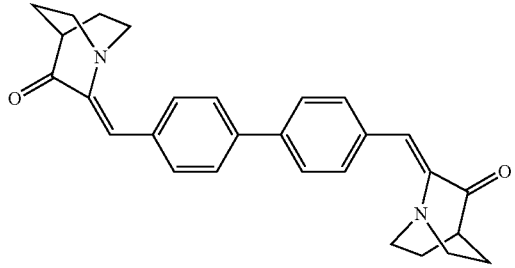

(14)

Quinuclidone hydrochloride (3.31 g, 0.02 mol) and potassium hydroxide (85%, 1.12 g, 0.02 mol) are dissolved in 50 ml of DMSO. A solution of biphenyl-4,4'-dicarbaldehyde (2.15 g, 0.01 mol) in 50 ml of DMSO is added dropwise to the mixture at 15° C. in the course of one hour. After the addition of a further portion of potassium hydroxide (1.12 g, 0.02 mol), the reaction suspension is stirred at room temperature for 16 hours. The crude product is then precipitated by the addition of 1M hydrochloric acid (200 ml) and, after filtration and washing with water, is recrystallised from a mixture of ethanol and chloroform (6:4). The product is dried in vacuo at 50° C.

Yield: 3 g (70%);

$\lambda_{max}$ (dioxane)=235 nm, 350 nm.

Example 14

Preparation of the Compound of Formula

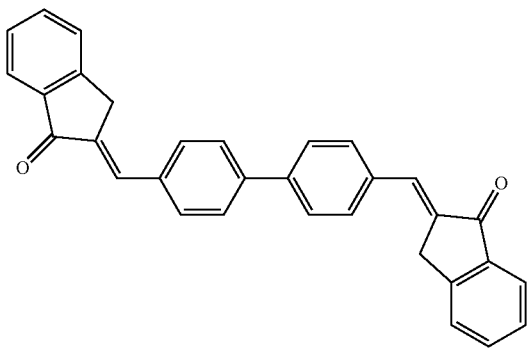

(15)

To a solution of biphenyl-4,4'-dicarbaldehyde (4.32 g, 0.02 mol) in 70 ml of DMSO and 10 ml of ethanol there are added dropwise, at 10° C., first potassium hydroxide (2.64 g) dissolved in 15 ml of ethanol and then, in the course of 15 minutes, a solution of 1-indanone (5.4 g) in 15 ml of ethanol. The reaction mixture is slowly heated to room temperature. After 3 hours' stirring, the reaction suspension is added to water (200 ml) and adjusted to a pH of 3 by the addition of 4N hydrochloric acid. The crude product is filtered off and washed with copious amounts of water and hot methanol. The product is dried in vacuo at 60° C.

Yield: 8.8 g (100%)

Elemental analysis: $C_{meas}$ 87.02% ($C_{calc}$ 87.65%), $H_{meas}$ 5.20% ($H_{calc}$ 5.06%).

Example 15

Preparation of the Compound of Formula

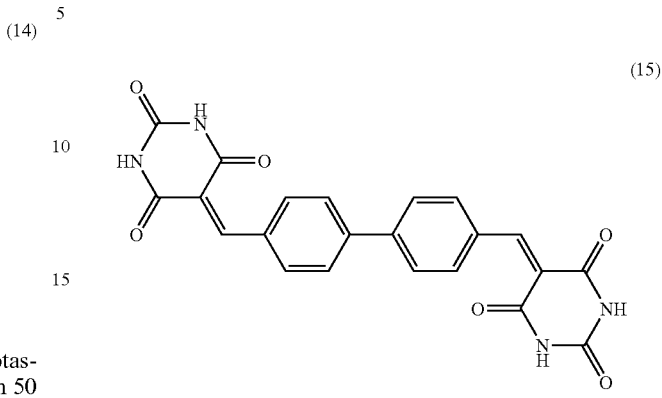

(15)

A mixture of biphenyl-4'-dicarbaldehyde (4.32 g, 0.02 mol), barbituric acid (5.43 g) and potassium fluoride (0.47 g) in 120 ml of ethanol is refluxed for 6 hours. After cooling to room temperature, the crude product is filtered off with 50 ml of ethanol and finally washed with 200 ml of hot water. The product is dried In a high vacuum at 60° C.

Yield: 7.8 g (89%);

$\lambda_{max}$ (DMSO)=396 nm, E (1%, 1 cm)=1134.

Example 16

Preparation of the Compound of Formula

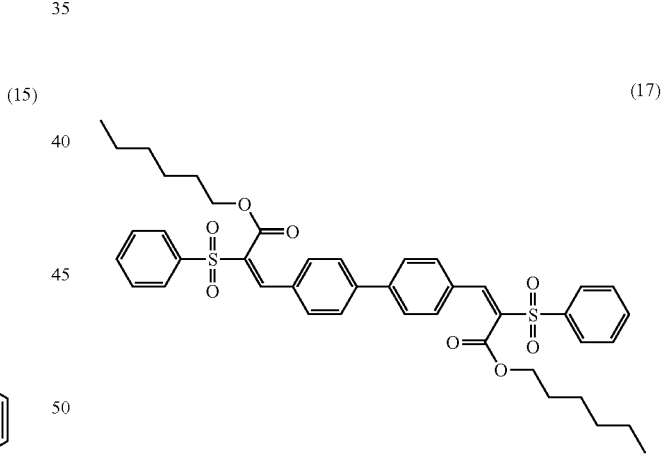

(17)

Phenylsulfonylacetic acid hexyl ester (4.23 g, 0.016 mol) and anhydrous potassium carbonate (1.12 g, 0.008 mol) are stirred in 10 ml of DMF for 30 minutes at room temperature under a nitrogen atmosphere. The mixture is then heated to 50° C., and a solution of biphenyl-4,4'-dicarbaldehyde (1.68 g, 0.008 mol) in 10 ml of DMF is then added dropwise in the course of 10 minutes. The reaction mixture is stirred for 16 hours at 50° C. After cooling to room temperature, the crude product is precipitated by the addition of 1M hydrochloric acid solution (40 ml) and, after filtration and washing with water, is recrystallised from a mixture of ethanol and DMSO (6:4). The product is dried in vacuo at 60° C.

Yield: 3.8 g (64%).

What is claimed is:

1. A compound of formula

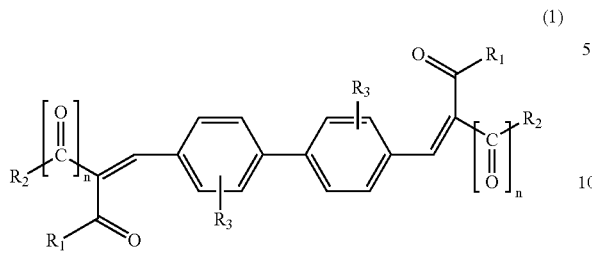
(1)

wherein
R$_1$ and R$_2$ together form a —(CH$_2$)$_{2-6}$— radical that is not further substituted or is substituted by one or more C$_1$-C$_5$alkyl and is uninterrupted or interrupted by one or two —O— and/or —NH— groups and/or

or
R$_1$ and R$_2$ together form the radical

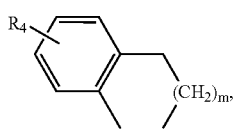

wherein
R$_4$ is hydrogen, C$_1$-C$_{10}$alkyl: or C$_1$-C$_{10}$alkoxy;
m is 0; or 1;
R$_3$ is hydrogen; C$_1$-C$_6$alkyl or C$_1$-C$_6$alkoxy; and
n is 0 or 1.

2. A compound according to claim 1, wherein
R$_1$ and R$_2$ together form a —(CH$_2$)$_{2-6}$— radical that is not further substituted or is substituted by one or more C$_1$-C$_5$alkyl and is uninterrupted or interrupted by one or two —O— and/or —NH— groups and/or

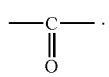

3. A compound according to claim 2, wherein
R$_1$ and R$_2$ together form an unsubstituted or C$_1$-C$_{10}$alkyl-substituted —(CH$_2$)$_4$— radical.

4. A compound according to claim 1, wherein
R$_1$ and R$_2$ together form the radical

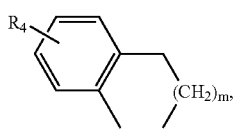

wherein
R$_4$ is hydrogen, C$_1$-C$_{10}$alkyl; or C$_1$-C$_{10}$alkoxy; and
m is 0; or 1.

5. A compound according to claim 1, wherein
R$_3$ is hydrogen.

6. A process for the preparation of a compound of formula (1) according to claim 1, which comprises reacting a diphenylbisaldehyde of formula

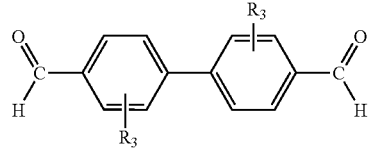
(1b)

wherein
R$_3$ is as defined for formula (1), in the presence of a base or an acid, with a compound of formula

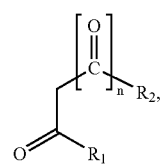
(1c)

wherein
R$_1$, R$_2$, R$_3$ and n are as defined in claim 1.

7. A method for the protection of human and animal hair and skin against UV radiation, which comprises contacting said hair and skin with an protectively effective amount of a biphenylene compound of formula (1)

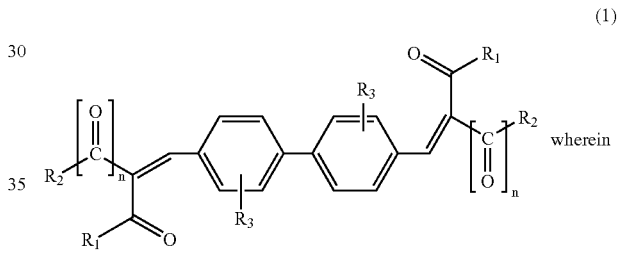
(1)

R$_1$ and R$_2$ together form a —(CH$_2$)$_{2-6}$— radical that is not further substituted or is substituted by one or more C$_1$-C$_5$alkyl and is uninterrupted or interrupted by one or two —O— and/or —NH— groups and/or

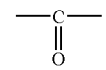

or R$_1$ and R$_2$ together form the radical

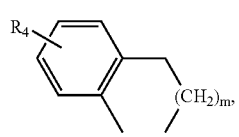

wherein
R$_4$ is hydrogen, C$_1$-C$_{10}$alkyl; or C$_1$-C$_{10}$alkoxy;
m is 0; or 1;
R$_3$ is hydrogen; C$_1$-C$_6$alkyl or C$_1$-C$_6$alkoxy; and
n is 0 or 1.

8. A method according to claim 7, wherein the biphenylene compound of formula (1) is in micronised form.

9. A cosmetic preparation comprising at least one or more compounds of formula (1) according to claim 1 together with cosmetically tolerable carriers or adjuvants.

10. A preparation according to claim 9 that comprises further UV protective agents.

* * * * *